United States Patent
Brännström (10) Patent No.: US 10,948,416 B2
(45) Date of Patent: Mar. 16, 2021

(54) METHOD AND APPARATUS FOR DETERMINING A CONCENTRATION OF A SUBSTANCE IN A LIQUID MEDIUM

(71) Applicant: BRÄNNSTRÖM GRUPPEN AB, Gothenburg (SE)

(72) Inventor: Roland Brännström, Gothenburg (SE)

(*) Notice: Subject to any disclaimer, the term of this patent is extended or adjusted under 35 U.S.C. 154(b) by 259 days.

(21) Appl. No.: 16/305,453

(22) PCT Filed: May 31, 2017

(86) PCT No.: PCT/SE2017/050582
§ 371 (c)(1),
(2) Date: Nov. 29, 2018

(87) PCT Pub. No.: WO2017/209685
PCT Pub. Date: Dec. 7, 2017

(65) Prior Publication Data
US 2020/0393379 A1 Dec. 17, 2020

(30) Foreign Application Priority Data

Jun. 3, 2016 (SE) .................. 1650784-0
Oct. 27, 2016 (SE) .................. 1651407-7

(51) Int. Cl.
*G01N 21/64* (2006.01)
*G01N 21/65* (2006.01)
(Continued)

(52) U.S. Cl.
CPC ............ *G01N 21/65* (2013.01); *G01N 21/64* (2013.01); *G01N 21/85* (2013.01); *G01N 33/1833* (2013.01); *G01N 2021/6421* (2013.01)

(58) Field of Classification Search
CPC ........... G01N 2021/6421; G01N 21/64; G01N 21/65; G01N 21/85; G01N 33/1833
See application file for complete search history.

(56) References Cited

U.S. PATENT DOCUMENTS 3,806,727 A 4/1974 Leonard et al.
4,555,179 A 11/1985 Langerholc et al.
(Continued)

FOREIGN PATENT DOCUMENTS

| CA | 2597000 A1 | 2/2008 |
|---|---|---|
| WO | WO-0140771 A2 | 6/2001 |
| WO | WO-2007143047 A1 | 12/2007 |

OTHER PUBLICATIONS

International Search Report and Written Opinion of the International Searching Authority issued in PCT/SE2017/050582, dated Aug. 30, 2017; ISA/SE.

*Primary Examiner* — Mark R Gaworecki
(74) *Attorney, Agent, or Firm* — Harness, Dickey & Pierce, P.L.C.

(57) ABSTRACT

The present invention relates to an apparatus for determining a concentration of a substance in a liquid medium of a test sample. The apparatus comprises a light source for directing a light beam of a first wavelength range towards the test sample, and a first detector for measuring intensity of irradiation emitted from the liquid medium at a second wavelength characteristic for the liquid medium. The apparatus further comprising a second detector for measuring intensity of irradiation emitted from the substance at a third wavelength characteristic for the substance, and a determining unit for determining the concentration of the substance in the liquid medium based on the measured intensities of the irradiation collected at the second wavelength and at the third wavelength.

14 Claims, 6 Drawing Sheets

(51) Int. Cl.
*G01N 21/85* (2006.01)
*G01N 33/18* (2006.01)

(56) References Cited

U.S. PATENT DOCUMENTS

| | | | |
|---|---|---|---|
| 8,575,541 B1* | 11/2013 | Jamison | G01N 21/85 |
| | | | 250/253 |
| 2003/0025909 A1 | 2/2003 | Hallstadius | |
| 2004/0161853 A1* | 8/2004 | Yang | A61B 5/0031 |
| | | | 436/164 |
| 2012/0018829 A1 | 1/2012 | Beck et al. | |
| 2015/0090900 A1 | 4/2015 | Banks et al. | |
| 2016/0282509 A1* | 9/2016 | Perkins | B32B 38/0004 |
| 2017/0184502 A1* | 6/2017 | Andrews | G01N 21/65 |
| 2017/0190946 A1* | 7/2017 | Pearl, Jr. | C09K 8/42 |
| 2018/0171781 A1* | 6/2018 | Price | G01V 8/14 |
| 2018/0275052 A1* | 9/2018 | Walsh | G01N 21/278 |

* cited by examiner

METHOD AND APPARATUS FOR DETERMINING A CONCENTRATION OF A SUBSTANCE IN A LIQUID MEDIUM

TECHNICAL FIELD

The present disclosure relates generally to a method and an apparatus for determining a concentration of a substance in a liquid medium of a test sample. Especially, the present disclosure relates to optically determining a concentration of a substance in a liquid medium of a test sample. The liquid medium may be water and the substance may be oil.

BACKGROUND

There are many application areas where it may be of interest to determine a concentration of a substance in a liquid medium. One such application area is for detecting oil concentration in water that is to be let out in the see from offshore platforms and large vessels. In offshore platforms, water and oil is pumped up, water is filtrated and let out into the sea again. Before the filtrated water is let out into the water, the remaining concentration of oil in the water is measured to determine that the concentration is not exceeding any prescribed limits, such as based on statutory regulations. The concentration of oil in water may be measured by an optical detector system where light is sent onto a sample containing water that may be mixed with oil, and light scattered from the sample is detected at wavelengths that are characteristic for oil and water.

U.S. Pat. No. 3,806,727 shows a prior art optical detector system where the oil pollution content of water is monitored by measuring the oil fluorescence spectrum scattered from a liquid sample comprising water polluted with oil, when being illuminated by an ultraviolet light source and by comparing the oil fluorescence spectrum with the Raman spectrum of water from the liquid sample. The sample is illuminated from a first direction and the scattered spectrum is detected at a second direction perpendicular to the first direction.

With such a system, however, it is difficult to correctly determine the concentration of oil in water when the sample contains a high percentage of particles, as the particles will reduce the amount of scattered irradiation that is detected. The particles may be e.g. oil forming lumps, which may occur when there are high concentration of oil in water, or the particles may be from other pollutants in the sample.

SUMMARY

It is an object of the invention to address at least some of the problems and issues outlined above. It is another object of embodiments to optically determine the concentration of a substance in a liquid medium with high precision. It is another object of embodiments of the invention to determine the concentration of a substance in a liquid medium of a test sample when the sample has high turbidity. It is another object of embodiments of the invention to monitor that the concentration is determined properly. It is another object of embodiments of the invention to determine when there is a risk that the concentration is not determined properly. It is possible to achieve these objects and others by using embodiments of a method and an apparatus as defined in the attached claims.

According to one aspect, an apparatus is provided for determining a concentration of a substance in a liquid medium of a test sample. The apparatus comprises a light source for directing a light beam of a first wavelength range towards the test sample, a first detector for collecting irradiation emitted from the liquid medium of the test sample as a result of the light beam directed towards the test sample, the irradiation being collected at one or more second wavelengths that are characteristic for the liquid medium, and for measuring an intensity of the irradiation collected at the one or more second wavelengths. The apparatus further comprises a second detector for collecting irradiation emitted from the substance of the test sample as a result of the light beam directed towards the test sample, the irradiation being collected at one or more third wavelengths that are characteristic for the substance, and for measuring an intensity of the irradiation collected at the one or more third wavelengths. The apparatus further comprises a determining unit for determining the concentration of the substance in the liquid medium of the test sample based on the measured intensity of the irradiation collected at the one or more third wavelengths and the measured intensity of the irradiation collected at the one or more second wavelengths. Further, the apparatus is arranged such that the irradiation collected by the first detector is emitted from a first surface area of the test sample and the irradiation collected by the second detector is emitted from a second surface area of the test sample, which first area and second area are at least partly covered by a surface area of the test sample illuminated by the light beam of the light source.

When trying to detect reflected light with the optical detector system of U.S. Pat. No. 3,806,727 light will tend to be absorbed in the test sample before it is emitted through the exit window that is 90 degree angled towards the incident window. This is especially true for turbid test samples as light travels much less distances until it is absorbed in samples with high turbidity than in samples with low turbidity. Consequently, the optical detector system of U.S. Pat. No. 3,806,727 cannot be used for turbid samples. However, by detecting irradiation emitted from surface areas of the test sample that are at least partly illuminated by the light beam of the light source, as in the present invention, e.g. the detected irradiation leaves the test sample at surface areas where the light from the light source entered the test sample, the reflected light can be strong enough to be detected, also for test samples having high turbidity.

The surface area of the test sample illuminated by the light beam of the light source may be called a light-entering area, or an illumination area. Further, the surface areas may be seen as an envelope surface of the test sample. For example, the illuminated area may be seen as the illuminated part of the total envelope surface of the test sample. The apparatus may be implemented in different ways to achieve that the areas of the test samples from which irradiation collected by the first and the second detector is emitted is at least partly illuminated by the light beam of the light source. Different possible examples of apparatus implementations are shown in the appended figures. According to an embodiment, the apparatus is arranged with light directing devices and light focusing devices so as to achieve that the irradiation collected by the first detector and the irradiation collected by the second detector is emitted from surface areas of the test sample that are at least partly covered by the surface area of the test sample illuminated by the light source. For example, light directing devices such as prisms and lenses may be used to see to that it is light reflected from a certain surface area that is received at the detectors. In a similar way, the light emitted by the light source may be focused by light directing devices such as lenses towards the light-entering surface area of the test so as to achieve an efficient and strong enough light onto a specified surface area of the test sample. There may be more than one light source directing light beams towards the samples.

According to an embodiment, the one or more second wavelengths related to the liquid medium is a wavelength of the Raman spectrum of the liquid medium. According to another embodiment, the one or more third wavelengths related to the substance is a wavelength of the Raman spectrum of the substance and/or a fluorescence spectrum of the substance. There may be more than one substance whose emitted irradiation is collected and measured by a detector.

According to an embodiment, the first detector and the second detector are arranged such that the first surface area and the second surface area are covered by the surface area of the test sample illuminated by the light beam of the light source. By illuminating a surface area of the test sample that covers the surface areas from which irradiation is collected by the detectors, emitted edge effects occurring at edges between illuminated and not illuminated surface areas are lowered. Such edge effects may have negative impact on the accuracy of the measurements of emitted irradiation. According to another embodiment, the illumination area not only covers the first surface area and the second surface area but also is larger than these areas. Hereby, edge effects are lowered even more.

According to another embodiment, the first surface area and the second surface area are substantially the same area. By arranging the apparatus so that the irradiation detected by the first detector and the irradiation detected by the second detector are emitted from the same or at least substantially the same surface area of the test sample, the accuracy of the measured intensities will increase. Especially, the mutual accuracy, in other words, the accuracy of the relation between the intensity of the irradiation detected by the first detector and the intensity of the irradiation detected by the second detector will increase when the different detected irradiation intensities originate from the same surface area of the test sample.

According to another embodiment, the first detector and the second detector are arranged symmetrically in relation to the light source. By arranging the first detector and the second detector symmetrically in relation to the light source, it is secured that emitted irradiation is detected by the first detector and the second detector from illuminated volumes, preferably described with cylindrical coordinates with its z-axis along the lighting direction, of the test samples that have the same irradiation intensity distribution in relation to radius and z-axis of the coordinate system. Hereby, accuracy of the concentration determination is secured. Further, according to an embodiment, the light source may produce a light cone that is symmetrical in regard to the z-axis. The first and the second detector may be arranged symmetrically in relation to the light source by positioning the first detector so that it receives reflected irradiation from the test sample that has a first angle towards the incident light from the light source and by positioning the second detector so that it receives reflected irradiation from the test sample that has a second angle towards the incident light from the light source, and that the first and the second angle have the same size, e.g. both first and second angle is 10 degrees.

According to another embodiment, the apparatus is arranged so that the first detector and the second detector receives irradiation emitted from the test sample at one and the same direction. Hereby it is secured that the first and second detector receives irradiation from the same illuminated surface area of the test sample. This may be achieved by receiving the emitted irradiation by for example a dichroic mirror or any other kind of device that reflects the second wavelength and lets the third wavelength through. The second detector may then be positioned so that it receives irradiation reflected by the device at the second wavelength and the third detector may be positioned so that it receives irradiation that is let through by the device at the third wavelength.

According to another embodiment, the apparatus is arranged so that there is a zero degree angle between the light beam directed towards the test sample and the irradiation emitted from the test sample that is received by the first detector and the second detector. Hereby it is achieved that the illuminated volume of the test sample is the same as the volume from which emitted irradiation is detected by the first as well as the second detector. Hereby, even more accurate measurement values can be achieved. An apparatus that is arranged in this way is described in FIG. 4. However, other similar apparatuses may achieve the same function, such as polarizing beam splitters being illuminated with monochromatic laser light. Responding irradiation in form of scattered depolarized light resulting from inelastic scattering will go straight through the beam splitter to the irradiation detector.

According to another embodiment, the first detector is further adapted to collect irradiation and measure intensity of the irradiation at the second wavelength, the irradiation being emitted from a reference sample comprising a known concentration of the substance in the liquid medium. Further, the second detector is adapted to collect irradiation and measure intensity of the irradiation at the third wavelength, the irradiation being emitted from the reference sample. Then, the determining unit is further adapted to determine the concentration of the substance in the liquid medium of the test sample based also on the measured intensity of the irradiation collected at the second wavelength from the reference sample and on the measured intensity of the irradiation collected at the third wavelength from the reference sample. By also taking into account measured intensity values for a reference sample having a known concentration of substance in liquid medium when determining the concentration of the substance in the liquid medium, the apparatus can be calibrated, thereby improving the accuracy of the concentration determination.

According to an embodiment, the apparatus further comprises a temperature sensor for detecting the temperature of the test sample. Further, the determining unit is arranged for determining the concentration of the substance in the liquid medium of the test sample based further on the detected temperature of the test sample. There is a temperature dependency between detected irradiation levels and the concentration of a substance in the medium. At room temperature, Raman scattering at a larger wavelength than the wavelength of the incident light, i.e. at a lower energy level, so called Stoke Raman, is much more common than Raman scattering at a shorter wavelength than the wavelength of incident light, so called anti-Stokes Raman. As the temperature increases, the Stokes Raman is decreased and the anti-Stokes Raman is increased. Knowledge of this temperature dependency can be used so that the actual temperature of the test sample is taken into consideration when determining the concentration of the substance in the medium of the test sample.

According to another embodiment, the liquid medium is water and the substance is oil.

Figure 1:
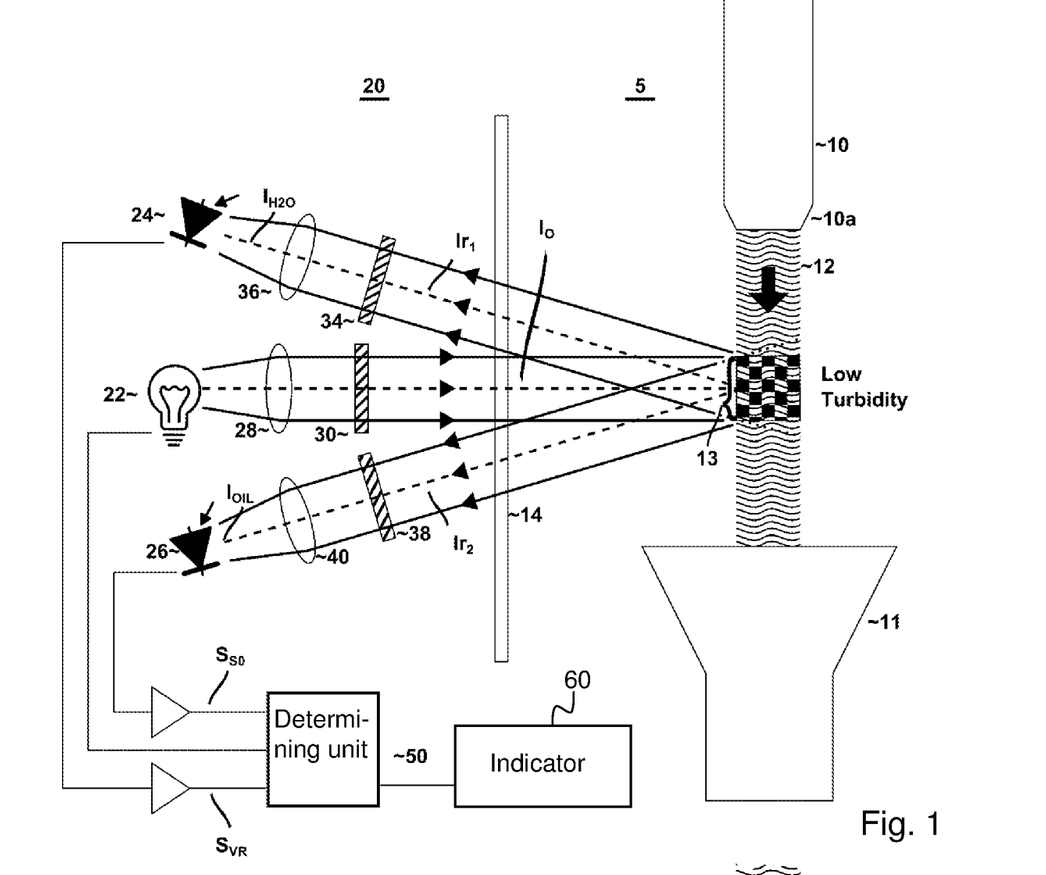
FIG. 1 is a schematic block diagram of an optical detector system in which the present invention may be used.

According to another embodiment, the apparatus further comprises an indicator for indicating when the measured intensity of the irradiation collected at the one or more second wavelengths is below a certain value. Hereby, it is possible to take actions in response to indication of irradiation from the liquid medium being below a level, for example a critical level, so as to stop a flow of test sample, divert the flow etc. The indicator may be a separate unit connected to the determining unit, as it is depicted in FIG. 1. However, the indicator may also be implemented in the determining unit.

According to an embodiment, the certain value is set so that when the measured intensity of the irradiation collected at the one or more second wavelengths is below the certain value, it is an indication of possible low concentration determining accuracy of the apparatus. When the measured intensity is below the certain value, it may be an indication that there may be a lack of, or loss of, sample in the apparatus, e.g. lack of sample flow. Alternatively, the test sample may be so turbid, or the share of liquid medium so low, and therefore the intensity of the irradiation from the liquid medium, e.g. water, is so low that the determination of the concentration of substance in medium becomes unreliable. The certain value is preferably preset, based on pre-requisites and constraints of the apparatus at manufacture. The certain value may be a set threshold value.

According to another embodiment, the indicator is arranged for indicating when the measured intensity of the irradiation collected at the one or more second wavelengths is below a certain value by issuing an alarm signal. The alarm signal may be an audible or visual alarm. For this reason, the apparatus may be equipped with a loudspeaker or a strong light-emitting lamp or similar, the loudspeaker or lamp being connected to the indicator. Such an alarm can cause personnel to act on the low level of liquid medium, by for example stopping the process flow.

According to another embodiment, the indicator is arranged for indicating when the measured intensity of the irradiation collected at the one or more second wavelengths is below a certain value by triggering a correction of a process flow system from which process flow the test sample is taken. The correction of the process flow system may be, for example, to automatically stop the process flow, or to set a valve of the system to change a direction of the process flow, from a first normal process direction to a second direction indicating a process problem. For example, when the process flow system is a system for controlling flow of waste water from a ship, the indication that the irradiation is below the certain value, would trigger a change of a valve so that the process flows into a holding tank instead of into the sea. Hereby, the process flow can be taken care of in a better way before it is sent out in the sea.

According to another aspect, a method is provided for determining a concentration of a substance in a liquid medium of a test sample. The method comprises directing a light beam of a first wavelength range towards the test sample, collecting irradiation emitted from the liquid medium of the test sample as a result of the light beam directed towards the test sample, the irradiation being collected at one or more second wavelengths that are characteristic for the liquid medium, and measuring an intensity of the irradiation collected at the one or more second wavelengths. The method further comprises collecting irradiation emitted from the substance of the test sample as a result of the light beam directed towards the test sample, the irradiation being collected at one or more third wavelengths that are characteristic for the substance, measuring an intensity of the irradiation collected at the one or more third wavelengths, and determining the concentration of the substance in the liquid medium of the test sample based on the measured intensity of the irradiation collected at the one or more third wavelengths and the measured intensity of the irradiation collected at the one or more second wavelengths. The method further comprises that the irradiation collected at the one or more second wavelengths is emitted from a first surface area of the test sample and the irradiation collected at the one or more third wavelengths is emitted from a second surface area of the test sample, which first area and second surface areas are at least partly covered by a surface area of the test sample illuminated by the light beam of the light source.

According to another embodiment, there are a plurality of substances in the liquid medium of the test sample. The method further comprises repeating the collecting and the measuring of intensities at the one or more third wavelengths for wavelengths characteristic for each of the plurality of substances. Further, the determining of the concentration of the plurality of substances in the liquid medium, for each of the plurality of substances.

Further possible features and benefits of this solution will become apparent from the detailed description below.

BRIEF DESCRIPTION OF DRAWINGS

The solution will now be described in more detail by means of exemplary embodiments and with reference to the accompanying drawings, in which:

FIGS. 3$a$-3$d$ are x-y diagrams showing substance concentration at their x-axis and measured intensity at their y-axis.

DETAILED DESCRIPTION

Briefly described, a solution is provided to optically determine the concentration of a substance in a liquid medium of a test sample, which solution is especially adapted for determining the concentration in test samples that has a high irradiation absorption coefficient, such as in turbid test samples. A high irradiation absorption coefficient signifies a short penetration depth for the irradiation, e.g. light. The irradiation absorption coefficient for the test sample depends on irradiation absorption coefficients for substances (including the liquid medium) that are situated in the test sample, and their respective concentrations in the test sample. The concentration of a substance in a liquid medium is determined by an apparatus comprising a light source arranged to direct irradiation in the form of light of a first wavelength range towards the test sample, and a first detector for detecting intensity of backscattered irradiation from the test sample at a second wavelength characteristic for the liquid medium, e.g. water, as a result of the light directed towards the test sample, and a second detector for detecting intensity of backscattered irradiation from the test sample at a third wavelength characteristic for the substance, e.g. oil. The concentration of the substance in the liquid medium is then determined based on the detected intensity of backscattered irradiation at the second wavelength and the detected intensity of backscattered irradiation at the third wavelength.

According to a first embodiment, for being able to get enough backscattered irradiation also from test samples that has high irradiation absorption coefficient, the irradiation detected by the first detector and the second detector is emitted from a surface area of the test sample that is illuminated by the light source. Hereby, the concentration of the substance in the liquid medium can be determined also for test samples having a very short irradiation penetration depth.

At tests of an apparatus for optically determining the concentration of a substance in a liquid medium, the inventor has observed that especially for low liquid medium response, i.e. when the amount of scattered, and consequently detected irradiation from the liquid medium is low, the accuracy of the apparatus is weakening. Such low amount of scattered irradiation from the liquid medium can be due to different reasons. For example, it could be due to high share of substance in the test sample, thus signifying low share of liquid medium in the test sample, and low share of liquid medium results in low amount of scattered irradiation originating from the liquid medium. Another reason may be that the test sample contains a substance that emits elastic reflections, i.e. that makes the test sample turbid. Elastic reflections signify that a high amount of the incident light is reflected at the surface or close to the surface of the test sample. Consequently, the incident light has a short penetration depth in the test sample and therefore the incident light only has the possibility to react with liquid medium at or close to the surface. As a result, there will be low amount of scattered irradiation originating from the liquid medium. Another reason may be that the test sample contains a substance, which is either measured or not measured, that emits strong inelastic reflections, e.g. strong fluorescence or Raman irradiation. As a result, the incident light has a short penetration depth in the test sample and therefore the incident light only has the possibility to react with liquid medium at or close to the surface. Another reason may be that there is a low amount of test sample in the apparatus, and low amount of test sample means low amount of liquid substance and therefore low scattered irradiation originating from the liquid medium. To be able to act on such possible weakened accuracy of the apparatus, the measured intensity of the reflected irradiation at the wavelengths characteristic of the liquid medium is observed. For this reason, and according to a second embodiment, the apparatus has been equipped with an indicator that indicates when the measured intensity of the irradiation from the liquid medium falls below a certain level, which level is set to be an indication of weakening accuracy of the apparatus. The indicator can trigger an alarm to get the attention of controlling personnel, or send a trigger signal to a valve of the water system that is controlled by the apparatus to e.g. shut off the flow of polluted water through the water system. The second embodiment may or may not be used together with the first embodiment.

An embodiment of an apparatus for determining concentration of a substance in a liquid medium is described in FIG. 1. The substance may be a liquid substance. In the following example the substance will be exemplified by oil and the liquid medium will be exemplified by water. A test sample 12 comprising oil mixed with water may be led through a wet part 5 of the apparatus, the wet part comprising a pipe 10 and a funnel 11. The pipe 10 may end in a tap 10a spaced apart from and arranged above the funnel 11 so that the water-oil mixture of the test sample falls in a free-falling jet from the pipe 10 until it is received in the funnel 11 arranged below the pipe. A light source 22 of a detecting part 20 of the apparatus is arranged so that light $I_0$ emitted from the light source will enter the test sample at a light-entering surface area 13 where the test sample falls in a free-falling jet from the pipe towards the funnel. In a not shown alternative, the sample may be led in a pipe also when it passes the light-entering area 13. In this alternative, the pipe 10 will have a transparent part through which the light beam may pass and come into contact with the sample. However, by arranging the wet part with a pipe and a funnel spaced apart so that the sample will fall in a free falling jet at the light-entering area, no such transparent part is needed, and the risk that this transparent part becomes dirty after being used some time is avoided. The light emitting and detecting part 20 comprises a collimator having at least one first convex lens 28 that focuses part of the light emitted by the LED 22 towards the light-entering area 13 of the wet part and a bandpass filter 30 that only lets a first wavelength range of the emitted light through, which first wavelength range is to be sent towards the light-entering area. The light emitting and detecting part 20, e.g. the LED 22 and the collimator may be arranged so that light entering area receives an extension that is not too small. For example, the LED and the collimator may be arranged so that the light-entering area receives a diameter approximately in the size of a path length, in the size of a possible incident light penetration depth into the sample, or in the size of a length of the sample in a direction of the incident light.

The light emitting and detecting part 20 comprises, except for the already mentioned light source 22, also a first detector 24 for detecting an intensity of irradiation at a second wavelength characteristic for water reflection, e.g. Raman reflection of water. The second wavelength is different from the first wavelength of the light entering the test sample at the light-entering area. The light emitting and detecting part 20 further comprises a second detector 26 for detecting an intensity of irradiation at a third wavelength characteristic for oil reflection, e.g. Raman reflection of oil. There may be more than two detectors for detecting other characteristics, for example different fluorescent-reflecting characteristics of oil. The respective first and second detector may be photo diodes. The light source 22 may be a Light Emitting Diode, LED. The emitted light may be in the ultraviolet, UV, range. The detecting part 20 further comprises a protection window 14 for letting through light/irradiation and preventing dirt to enter the detecting part 20.

As the incoming light $I_0$ falls onto the test sample 12, elements of the test sample will reflect, or scatter, the incoming light. A small fraction of the reflected irradiance is the result of inelastic scattering, i.e. that the scattered particles have an energy that is lower and/or possibly higher than the energy of the photons falling onto the test sample. The inelastic scattered irradiance is characteristic for the substance that received the incoming photon and that sent out the inelastic scattered irradiance. Fluorescence and Raman scattering are results of such inelastic scattering. The inelastic scattered irradiance is omnidirectional. A part of the inelastic scattered irradiance will be reflected back towards the first detector 24 and towards the second detector 26. Before falling onto the first detector 24, the reflected irradiance $I_{r1}$ passes through a bandpass filter 34 that only lets through wavelengths characteristic for inelastic scattering of water, such as the Raman reflection of water. Hereby, elastic scattering wavelengths as well as other inelastic scattering wavelengths are filtered out. The irradiance of the wavelengths for inelastic scattering of water is further received by an objective 36 comprising one or more lenses to concentrate the irradiance towards the photo diode 24 that determines the intensity of the inelastic scattered irradiance of water, e.g. the Raman reflection. The intensity may be determined by determining an energy level or power level of the received irradiance. The first detector is positioned so that the intensity resulting from irradiance due to inelastic scattering of water $I_{H2O}$ it receives is emitted from a surface area of the test sample that is covered by the light-entering area 13. The optics of the apparatus, i.e. the objective 36 of the first detector is arranged so that it is the scattered irradiance received from a surface area of the test sample covered by the light-entering area 13 that is received by the photo diode 24.

Before falling onto the second detector 26, the reflected irradiance $I_{r2}$ is passed through a bandpass filter 38 that only lets through wavelengths characteristic for inelastic scattering of oil, such as the Raman reflection or fluorescence of oil. Hereby, elastic scattering wavelengths as well as other inelastic scattering wavelengths are filtered out. The irradiation of the wavelengths for inelastic scattering of oil is further received by an objective 40 comprising one or more lenses to concentrate the irradiation towards the photo diode 26 that determines the intensity of the inelastic scattered irradiance of oil. The second detector is positioned so that the intensity resulting from irradiance due to inelastic scattering of oil $I_{oil}$ it receives is emitted from a surface area of the test sample that is covered by the light-entering area 13. The optics of the apparatus, i.e. the objective 40 of the second detector is arranged so that it is the scattered irradiance received from a surface area of the test sample covered by the light-entering area 13 that is received by the photo diode 26.

Information on the determined intensity of inelastic scattered irradiance of oil and information on the determined intensity of inelastic scattered irradiance of water are sent to a determining unit 50 that determines the concentration of oil in water based on the received information. The determined intensity may be a level of signal strength, power or energy.

In the prior art solution of U.S. Pat. No. 3,806,727, the concentration of oil in water is determined by comparing the oil fluorescence spectrum with the Raman spectrum of water from the liquid sample. However, such a determination does not give a correct determination of the concentration, especially not when the test sample has a high irradiation absorption coefficient. This could be understood when looking at the curve of FIG. 2 of U.S. Pat. No. 3,806,727, wherein the intensity ratio flattens out with increasing oil concentration.

The apparatus of FIG. 1 also comprises an indicator 60. The indicator of the apparatus of FIG. 1 is connected to the determining unit 50. However, in another embodiment, the indicator 60 may also be directly connected to the photo diode 24. The indicator 60 may alternatively be a part of the determining unit 50. The indicator 60 is arranged to indicate when the intensity of the inelastic scattered irradiance of water determined by the photo diode 24 is below a preset level, which level indicates possible low concentration determining accuracy of the apparatus. The comparison between the intensity determined by the photo diode 24 and the preset level may be performed in the indicator 60 itself or in the determining unit 50. The indicator 60 may comprise an alarm unit that triggers an alarm signal when the intensity determined by the photo diode 24 is below, or falls below, the preset level. The alarm signal may be directed to a loudspeaker or similar through which an audible alarm signal is issued. Alternatively, or in addition, the alarm signal may be directed to a light alarm signal, such as a light emitting unit emitting e.g. sharp blinking light to catch the attention of the surroundings. Alternatively, or in addition, the alarm signal may be sent to a control unit controlling a process flow, from which process flow the test sample is taken. The control unit may take actions when receiving the alarm signal, such as shutting off the process flow comprising the liquid medium mixed with the substance or diverting the process flow to an alternative route. Alternatively, the signal sent from the indicator 60 may be used to directly shut off or divert the process flow. The indicator may also be used for indicating a high concentration of substance in the liquid medium, for example when the concentration is higher than an allowed value for pollutants, or a value acceptable by the owner of the process flow.

A test sample may comprise, except for the liquid medium and one or more substances (sometimes called target substances) to be detected, also disturbance substances, which concentrations are not to be detected but that may influence the irradiation reflections due to inelastic scattering as the disturbance substances may absorb incident light and/or reflected irradiation During the following assessment, it is assumed only insignificant change of content of liquid medium, i.e. water, and a constant content of target substance related to the second detector 26, i.e. oil. Intensity of the scattered irradiation that is detected at the first and second detectors 24, 26 then depends on the intensity sent from the light source and the proportions of disturbance substances which affects the proportion of water and the proportion of the target substance respectively that gives rise to the inelastic scattering The penetration of incident light in the test sample, called penetration depth, changes when the test sample's content of disturbance substances is changed. When the content of disturbance substances is decreased, the penetration depth is increased, and vice versa. With an increased penetration depth, more molecules of oil and water will be excited per unit time resulting in higher amount of inelastic scattering. Independent on the actual penetration depth it will be a proportionally same change in inelastic scattering for oil and water as well as for other substances in the test sample, i.e. the proportion of water and the proportion of oil that gives rise to the inelastic scattering will both change in the same proportion to the penetration depth. The ratio between irradiation detected at the first and second detectors 24, 26 will thus be constant for a constant content of target substance related to the water content independent on the actual penetration depth.

Figure 2:
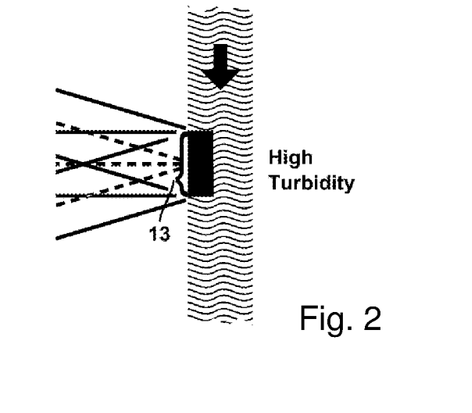
FIG. 2 is a schematic block diagram illustrating penetration depth in an optical detector system as in FIG. 1 for light falling onto a sample having high turbidity in relation to a sample having low turbidity illustrated in FIG. 1.

FIG. 2 shows a possible penetration depth in a sample having high absorption coefficient, i.e. high turbidity. As can be seen, the incident light only reaches a short distance below the surface. As a consequence, the intensity of inelastic scattering from both water and oil will be lower in FIG. 2 compared to in FIG. 1, which shows possible penetration depth in a sample having low absorption coefficient, i.e. low turbidity. As could be understood for the system of U.S. Pat. No. 3,806,727, when seeing the short penetration depth of the sample of high turbidity of FIG. 2, there will be very little irradiation, if any that would have gone through the sample and out at the 90 degree angle for such a turbid sample. In other words, in a test sample that has disturbance substances giving the test sample a high absorption coefficient, i.e. a short penetration depth, the concentration of a target substance in a liquid medium cannot be determined by the prior art system.

A similar problem may occur if the concentration of the substance, e.g. oil, detected by the second detector becomes high. Here it is assumed that the content of disturbance substances, the content of target substances not detected by the second detector, as well as the content of water is approximately constant. Then the irradiation absorption coefficient of the sample is mainly determined by the irradiation absorption coefficient of the target substance. In other words, the penetration depth will be lowered as the concentration of the target substance increases. When the concentration of the substance increases, the incident light falling onto the liquid medium, e.g. water will be lower. Consequently, the reflected irradiation $I_{H2O}$ falling onto the first detector 24 will decrease as the concentration of the target substance increases. In the same way, the incident light falling onto the substance increases with increased substance concentration, however, as the substance concentration increases, the penetration depth decreases. When the absorption coefficient for the target substance is higher than the sum of absorption coefficients for other substances in the sample and also higher than 1/path length, $I_{oil}$ flattens out, alternatively reaches a maximum limit. The maximum limit could be seen e.g. in the dashed-dotted curve of FIG. 3a. Consequently, for substance concentrations that results in a high absorption coefficient for the test sample, the penetration depth in the sample is low and the same problem of receiving enough light will occur for the system of U.S. Pat. No. 3,806,727 as when there are disturbance substances in the test sample.

Consequently, an apparatus as shown in FIG. 1, where a surface area of the test sample from which irradiation is reflected as a result of inelastic scattering and detected by the first detector 24 and the second detector 26 is at least partly covered by a surface area of the test sample illuminated by the light originating from the light source 22, receives much more scattered irradiation and therefore a better accuracy compared to the system of U.S. Pat. No. 3,806,727.

According to an embodiment, the first detector 24 and the second detector 26 are arranged symmetrically around the light source 22. In the embodiment of FIG. 1 the first detector is positioned opposite the second detector with the light source arranged in between the first and the second detector. The distance between the first detector and the light source is the same as the distance between the second detector and the light source. In other words, the angle between light $I_0$ falling onto the test sample and irradiation $I_{r1}$ emitted by the test sample and detected by the first detector is the same as the angle between light $I_0$ falling onto the test sample and irradiation $I_{r2}$ emitted by the test sample and detected by the second detector.

The following simplified formula demonstrates the properties of the apparatus for determining the absorption coefficient $k_{Si}$ of a substance i in a liquid medium.

$$k_{Si} = B_{Si} \frac{\Phi_{Si}}{\Phi_{VR}} \left(1 - \varphi_{SC} - \sum_{m=0}^{j} \varphi_{Sm}\right) \quad \text{Eq. (20)}$$

$$i \in 0, 1, \ldots j$$

All $\varphi_{Sm}$ of Eq. (20) can be substituted by detected light flows $\Phi_{Sm}$ m∈0, 1, ..., j and adapting constants.

In Eq. (20), $\Phi_{S1}$ and $\Phi_{Sm}$ are detected response as light flux (i.e. inelastic scattered intensity) from substance i, alternatively m. $\Phi_{Si}=\Phi_{Sm}$ for i=m, $\Phi_{VR}$ is detected response as light flux from the liquid medium, $\varphi_{Sm}$ and $\Phi_{S1}$ are volume share of substance i alternatively m. $\varphi_{Si}=\varphi_{Sm}$ for i=m, $\varphi_{SC}$ is volume share of disturbance substance, $k_{S1}$ is an absorption coefficient for substance i, $B_{S1}$ is a constant determined by calibration of the apparatus.

An assumption in this formula may be that one or more of the following constraints are fulfilled: $\phi_{S1}$ is the only essential response from substance i and $\phi_{VR}$ is the only essential response from the liquid medium; the absorption coefficient of the liquid medium is less than the inverse of the path length; that the temperature is constant; that the densities of the substances are not changed due to mixing relations in the test sample; that substances are not reduced or are added due to chemical reactions; that all substances in the sample influencing the volumes are included in the measurements or in $\varphi_{Sc}$; that the solution is homogeneous and that the particle size distribution and properties are constant independent of their concentration. Disturbance substances should not direct give any significant response $\phi_{S1}$ for any of the j+1 substances at their respective detectors or any significant response $\phi_{VR}$ at the detector for the liquid medium. Indirect all $\phi_{S1}$ and $\phi_{VR}$ responses will be affected due to the change of the total sum of absorption coefficients. The disturbance substances are not going to disturb the measurement on the substances i in any other way than that the measurement precision may be lower as the absorption coefficient for the disturbance substance SC increases, as the amount of back-scattered irradiation from the medium and the substances i decreases with increasing absorption of the disturbance substance.

Figure 3A:
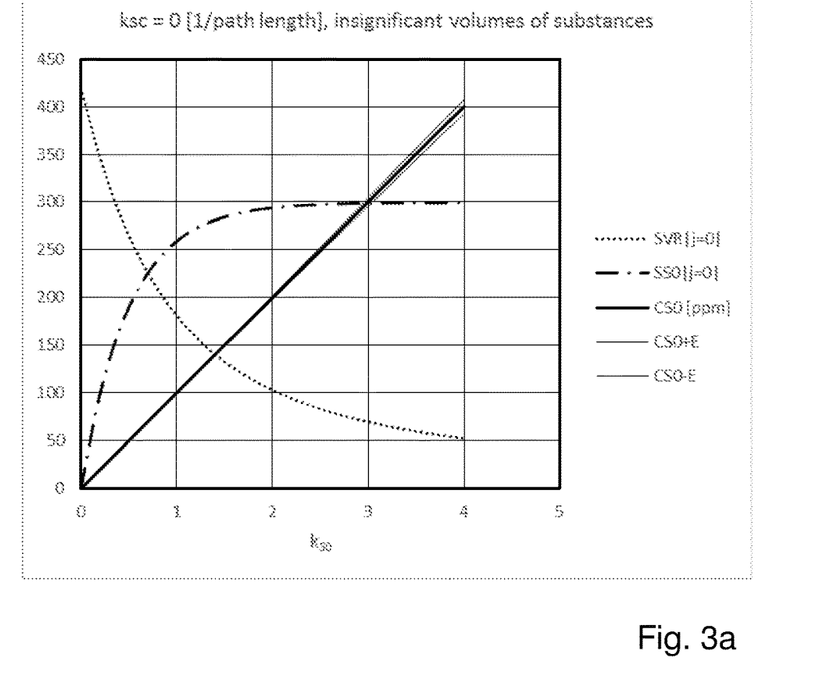
Figure 3B:
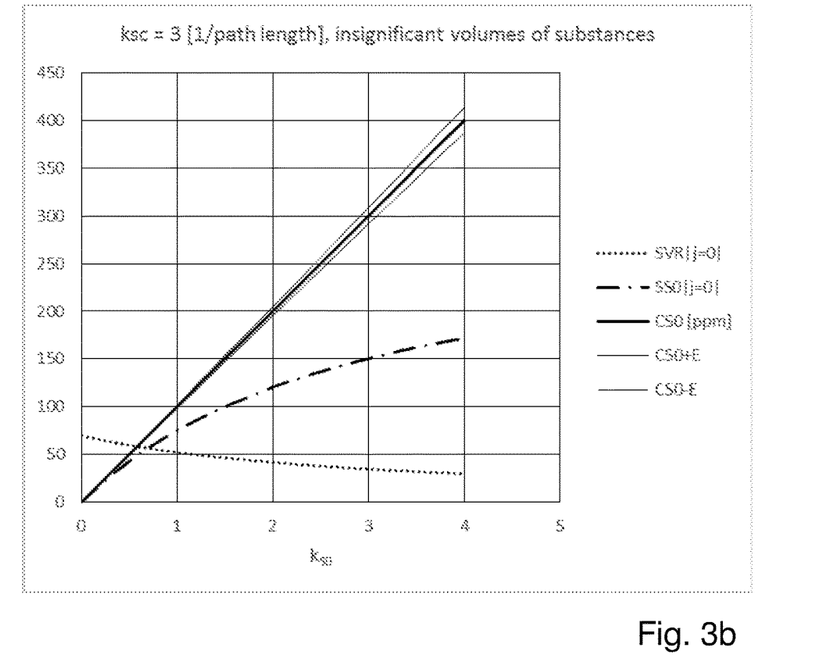
Figure 3C:
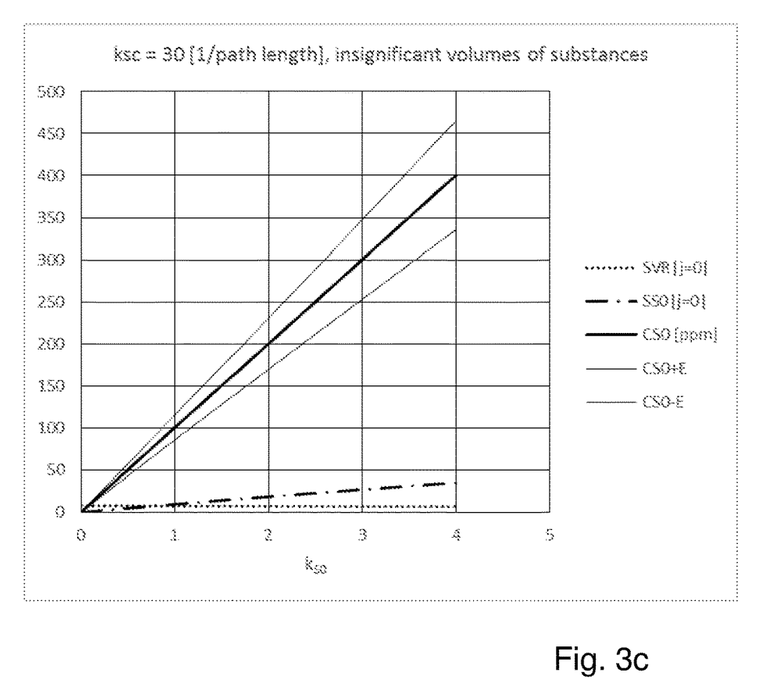

The diagrams of FIGS. 3a-c show experimental calculations for determining the concentration CS0 of a substance S0 in a test sample comprising the substance S0, a liquid medium that in this example is water, and one or more disturbance substances SC. In the calculations of FIGS. 3a-3c, the substance S0 constitutes an insignificant volume share in water compared to the amount of water. The concentration CS0 is shown on the y-axes as parts per million, PPM, $k_{S0}$ on the x-axes signifies the absorption coefficient of the substance S0. The concentration CS0 of the substance S0 is determined based on detected water Raman, $S_{VR}$, and detected substance response for the substance S0, $S_{S0}$ (such as oil Raman). Increasing absorption coefficient $k_{SC}$ due to disturbing substances will reduce both $S_{VR}$ and $S_{S0}$ response. $k_{S0}$ on the x-axis signifies the real concentration of the substance in water provided that a conversion factor to concentration is known, given that all parameters are constant except absorption coefficient $k_{S0}$ for the substance S0. An increase of the absorption coefficient $k_{S0}$ for the substance S0 signifies that the substance S0 has more inelastic scattering in the wavelengths where the substance response is detected, and therefore an increased substance response, provided that all other parameters are constant. Increased absorption coefficient $k_{S0}$ in the experimental calculations may be seen as a way of simulating an increase of the substance degree in the test sample.

The absorption coefficient $k_{SC}$ of the disturbance substance may be seen as the turbidity of the test sample, KSC=1 signifies that the absorption coefficient due to turbidity is 1/path length. KSC=0 signifies a clear test sample having no turbidity from disturbing substances. The turbidity then increases with increased absorption coefficient. FIG. 3a shows experimental results for $k_{SC}=0$, i.e. for a sample not affected by turbidity from disturbing substances. FIG. 3b shows experimental results for $k_{SC}=3$, i.e. a sample with a rather high turbidity from disturbing substances. FIG. 3c shows experimental results for $k_{SC}$=30, i.e. a sample with very high turbidity from disturbing substances. In all of the FIGS. 3a to 3c the disturbance substance constitutes an insignificant volume share. Further, it is seen from the figures that the detected water Raman $S_{VR}$ is decreased as the absorption coefficient $k_{S0}$ of the substance S0 in water is increased while the detected substance S0 response is increased as the absorption coefficient $K_{S0}$ of the substance is increased. The experimental calculations show that there is a constant ratio between detected water Raman $S_{VR}$ and detected substance S0 response Ss0 which is proportional to the determined concentration. Consequently, $C_{S0} \propto {}^*S_{S0}/S_{VR}$. This relation is also valid when the turbidity increases, as can be seen in FIGS. 3b and 3c. Further, as shown by the lines Cs0+E and Cs0−E in the right diagrams of FIGS. 3a-3c, E signifying a possible standard deviation, the measurement accuracy is decreased for increased turbidity. This is due to the lowered determined water Raman levels and substance response levels due to increased absorption coefficient $k_{SC}$ for disturbance substances as the turbidity increases. This accuracy limitation does not have anything to do with the principle. Instead it is related to measuring accuracy limitations. The disturbance substances SC may be particles or substances that dissolves in water, or a combination thereof.

Figure 3D:
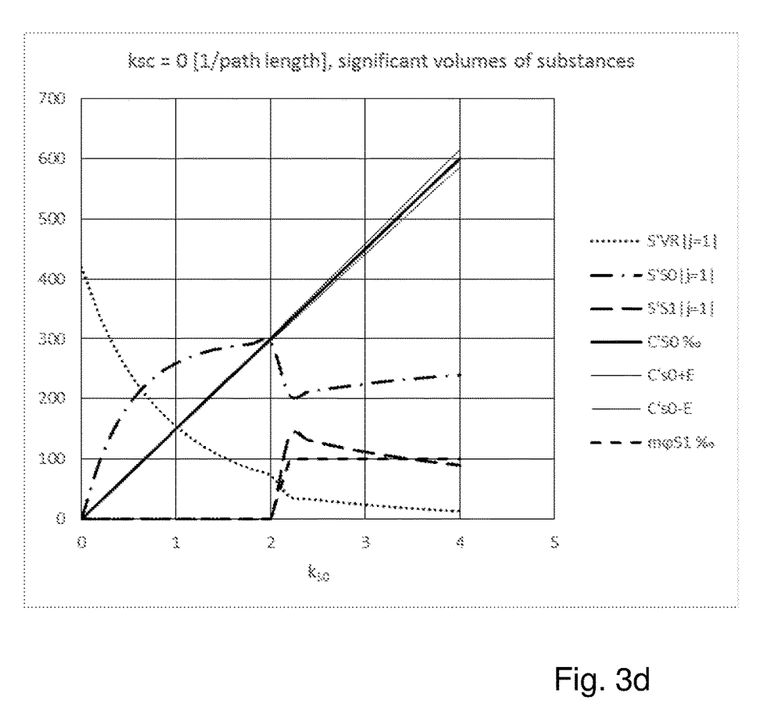

FIG. 3d shows experimental calculations for determining the concentration $C'_{S0}$ of a substance S0 in a test sample comprising a substance S0, a liquid medium that in this example is water, a second substance S1 that also is detected and one or more disturbance substances SC. Compared to the calculations of FIG. 3c, the concentration of target substances S0 and S1 in FIG. 3d has a significant volume share in relation to the volume share of water. Please observe that the concentration of substance in water on the y-axis is in per thousand this time and not in ppm as for FIGS. 3a-3c. In FIG. 3d, the absorption coefficient for the disturbance substance $k_{SC}$ is set to =0, signifying no absorption from disturbance substances. In the experiment of FIG. 3d, the x-axis follows a chronological order. Firstly, substance S0 is added until $k_{S0}$=2, i.e. 30% concentration of $S_0$ in the sample. Then, substance S0 and S1 is added so that the concentration becomes 60% water, 30% S0 and 10% S1. The substances S0 as well as S1 have a higher absorption coefficient than water. Therefore, the detected response $S'_{S0}$ for the first substance S0 becomes weaker when the second substance S1 is added, seen in the FIG. 3d at $k_{S0}$=2. At $k_{S0}$=2, the adding of S1 can also be seen, as the detected response $S'_{S1}$ for the second substance S1 goes from 0 to over 100. Also, the detected water Raman $S'_{VR}$ becomes weaker, as there is less light for water to reflect. After the adding of substance S1, substance S0 is added in such a way that water is replaced by S0 until $C'_{S0}$ becomes 60%. However, the relation $S'_{S0}/S'_{VR}$ is still maintained, as could be seen by the straight line $C'_{S0}$.

Figure 4:
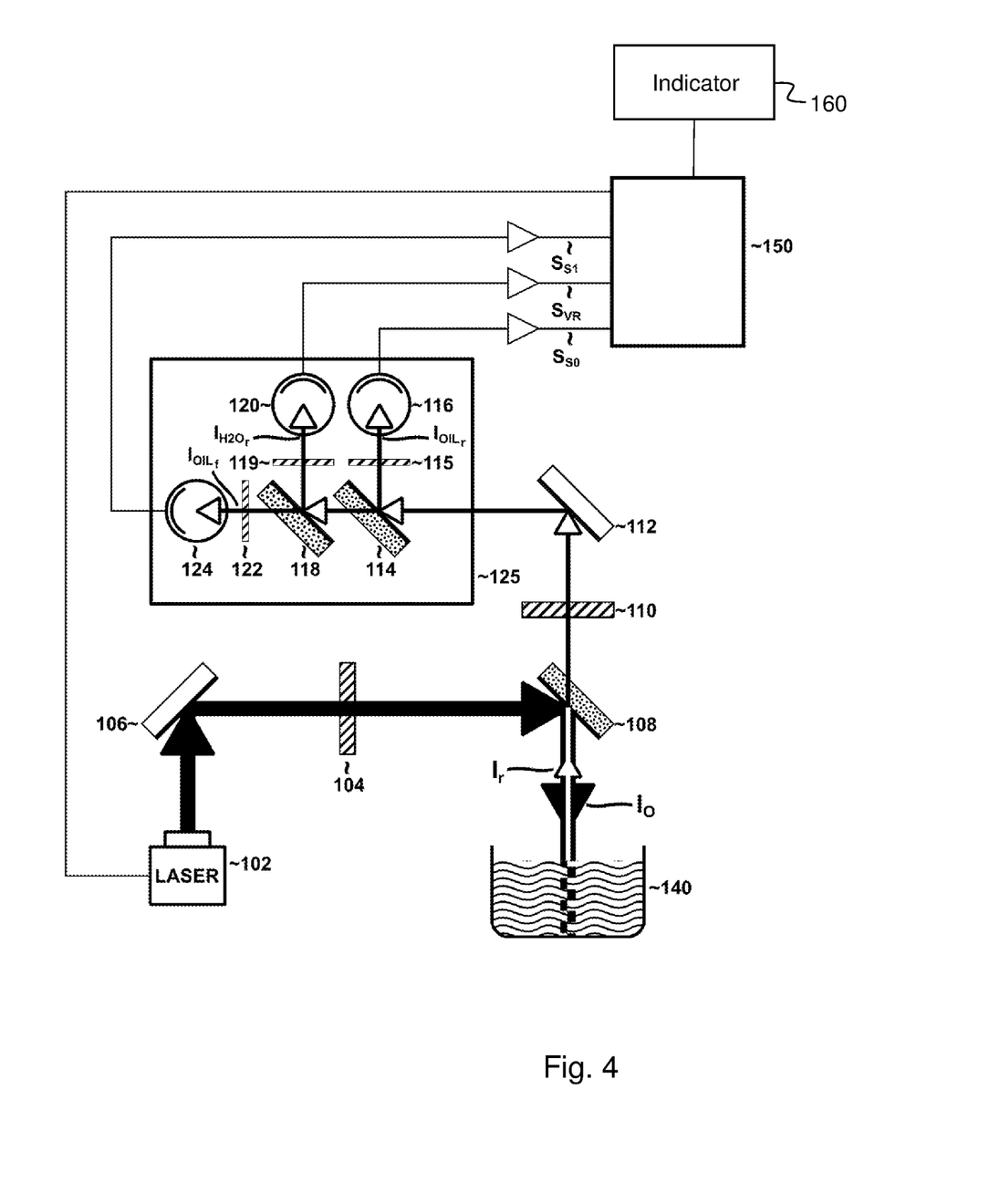
FIG. 4 is a schematic block diagram of another optical detector system in which the present invention may be used.

FIG. 4 shows another embodiment of an apparatus for determining concentration of a substance in a liquid medium. This apparatus has a zero degree angle between incident light and reflected light, as could be seen from the figure. This is achieved by the use of dichroic mirrors. Dichroic mirrors are arranged to reflect certain wavelengths while other wavelengths passes through the mirror. However, other technologies similar to dichroic mirrors for achieving incident and reflected light having a mutual angle of zero degrees may also be used. The apparatus of FIG. 4 comprises a light source 102 in the shape of e.g. a solid state laser that emits light of a certain wavelength or wavelength range. The apparatus further comprises a first mirror 106 that may be adjustable and that is arranged to reflect light originating from the light source 102 towards a first dichroic mirror 108. The first dichroic mirror 108 is arranged to reflect light reflected from the first mirror 106 that is of a first wavelength range so that the light of the first wavelength range falls as incident light $I_0$ onto a test sample 140 comprising a liquid medium in which there is a substance. Light of wavelengths outside the first wavelength range passes through the first dichroic mirror 108. The apparatus may further have an optional neutral density filter 104 and/or a line filter arranged between the first mirror 106 and the first dichroic mirror 108. The neutral density filter and the line filter are arranged to filter out undesired wavelengths before the desired first wavelength range is reflected in the first dichroic mirror. Any or some of the light source 102, the first mirror 106 and the first dichroic mirror 108 as well as the optional filter 104 are arranged so that incident light is concentrated towards a light-entering area of the test sample. The light-entering area has characteristics similar to the light-entering area of the embodiment of FIG. 1. In a similar way, the reflected and eventually detected irradiance has characteristics similar to the embodiment of FIG. 1, i.e. such that the irradiation collected by the first detector is emitted from a first surface area of the test sample and the irradiation collected by the second detector is emitted from a second surface area of the test sample, which first area and second area are at least partly covered by a surface area of the test sample illuminated by the light beam of the light source.

The incident light is then inelastically and possibly also elastically reflected by the liquid medium and the substance in the same way as explained earlier. The inelastic reflections are characteristic for the materials in the sample, i.e. for the liquid medium and the substance, which means that the inelastic reflections have a different wavelength than the first wavelength range of the incident light, if the first wavelength range is selected to be outside the sample characteristic wavelengths. Elastic reflections are mainly the reflections of the laser beam, i.e. having the first wavelength range of the incident light $I_0$. The first dichroic mirror 108 receives reflected irradiation $I_r$ from the sample and since it is arranged to let wavelengths different than the first wavelength range through, it will let the reflected irradiation due to inelastic reflection through while any possible elastic reflection having the first wavelength range is reflected by the mirror 108. The apparatus then further comprises a blocking filter 110 that is arranged to block wavelengths that are not to be analyzed by the apparatus but let wavelengths characteristic for the inelastic reflection of the medium and the substance through. The wavelengths let through the blocking filter are reflected by a second mirror 112 towards an irradiation detector 125 of the apparatus. The irradiation detector 125 comprises a second dichroic mirror 114 that is arranged to reflect irradiation of a second wavelength characteristic for inelastic reflection of the medium or the substance, e.g. Raman reflection of oil. Light of the second wavelength is then led through a blocking filter 115 to further filter out any wavelengths outside the second wavelength and ends up in a first photomultiplier tube, PMT, 116 that detects the incoming irradiation intensity, or level. A PMT is adapted to detect low irradiation levels, such as the levels from Raman reflection and fluorescence. The irradiation detector 125 further comprises a third dichroic mirror 118 that is arranged to reflect irradiation of a third wavelength characteristic for inelastic reflection of the one of the medium and the substance which irradiation was not reflected by the first dichroic mirror 114, e.g. Raman reflection of water. The detector 125 further comprises a blocking filter 119 to further filter out any wavelengths outside the third wavelength and a second PMT 120 for detecting the incoming irradiation level of the third wavelength. The irradiation detector may also comprise another filter 122 for filtering out an additional wavelength that has passed through both the second dichroic mirror 114 and the third dichroic mirror 118 of the irradiation detector, and a third PMT 124 for detecting an incoming irradiation level of the additional wavelength. The additional wavelength may be characteristic for a fluorescence of the substance, i.e. fluorescence reflection of oil for example, if the Raman reflection of the substance was detected by the first or the second PMT. Alternatively, the additional wavelength may be characteristic for a second substance of the test sample, in case there are more than one substance in the test sample, which concentration is of interest to determine. The detector 125 may also be a spectrophotometer of some type detecting energies at the required wavelengths.

Information on the determined intensity of inelastic scattered irradiance of liquid medium and information on the determined intensity of inelastic scattered irradiance of substance, as well as information on determined intensity at the additional wavelength, if used, are sent from the respective PMT 116, 120, 124 to a determining unit 150 that determines the concentration of substance in liquid medium based on the received information. The determined intensity may be a level of signal strength, power or energy The test sample of FIG. 4 is shown as being in a bowl or similar that is filled with the test sample. However, the test sample may be brought into the apparatus in the same way as was performed in the apparatus of FIG. 1, i.e. as a free falling jet falling from a pipe 10 into a funnel 12. The test sample may be a divergence from a process flow that is monitored, such as a bleed-off or bypass from the process flow. In a similar way, the detecting part 20 of the apparatus of FIG. 1 may be used together with a bowl or similar that is filled with the test sample, as in the FIG. 4 apparatus.

The apparatus may need to be calibrated as there are a number of parameters that influences the measurements. An expedient way of calibrating the apparatus may be to use a reference sample where there is a known concentration of substance in a medium. The reference sample is then used in an apparatus as the one described in FIG. 1 or FIG. 4. The first detector 24; 116 collects irradiation at the second wavelength and measures the intensity of the collected irradiation. The second detector 26; 120 collects irradiation at the third wavelength and measures the intensity of the collected irradiation. Now measurement values have been received for a known concentration and the unbroken line of FIGS. 3a-3d could be calibrated taking into account that the unbroken line should pass the coordinate origin. A possible way of performing the calibration when using the embodiment of FIG. 1 is to replace the free falling jet with a container or bowl comprising the reference sample. The reference sample is then to be positioned at the same distance as the free falling jet was. Even though the best calibration would occur if the reference sample is introduced in the wet part 5 it may be difficult to replace the test sample with the reference sample, and in that case, such a calibration using a bowl, container or similar in which the reference sample resides is much easier to handle.

In the following a short mathematical description is provided for calibrating the apparatus for detection of concentration of substances S1 for $i \in 0, 1, \ldots, j$ using inelastic scattering detection. For all i, measure flux for substances Si for a reference sample, $\Phi_{Si|CALIBm|}$, flux for water Raman for the reference sample, $\Phi_{VR|CALIBm|}$ and volume share for substance Si for reference sample, $\varphi_{Si|CALIBm|}$ for reference samples having a medium with a substance S1 that have a known absorption coefficient $k_{Si|CALIBm|}$ that may be approximately 1 per inverse of path length but with a volume share below 50%. |CALIBm| refers to calibration event m. Preferably, the reference samples should be clean, i.e. for substance i of calibration event m where m=i the following relationship should apply;

$k_{Si|CALIBm|} \gg (k_{SC|CALIBm|} + k_{VR|CALIBm|} + \Sigma_{i=0;m \neq i}^{j} k_{Si|CALIBm|})$ for achieving a good result.

$k_{SC|CALIBm|}$ is the absorption coefficient of the disturbance substance and $k_{VR|CALIBm|}$ is the absorption coefficient of the liquid medium. Further provided that substance m only insignificantly affects other detectors than detector m during calibration event m which implies that $\Phi_{Sm|CALIBm|} \gg \Phi_{Si|CALIBm|}$ m≠i and that the sample is clean, that is $\varphi_{Si|CALIBm|} = 0$ for all m≠i and $\varphi_{SC|CALIBm|} = 0$, equation (20) can be reshaped and applied;

$$k_{Si} \frac{\Phi_{VR}}{1 - \varphi_{Si}} = B_{Si} \Phi_{Si}$$

$$i \in 0, 1, \ldots j$$

Divided in calibration events indexed m this results in;

$$\frac{k_{Si|CALIBm|} \Phi_{VR|CALIBm|}}{(1 - \varphi_{Si|CALIBm|})} = B_{Si} \Phi_{Si|CALIBm|} \qquad \text{Eq (20a)}$$

$$m = i$$

or;

$$(B_{|CALIBm|} =) B_{Si} = \frac{1}{(1 - \varphi_{Si|CALIBm|})} \frac{\Phi_{VR|CALIBm|}}{\Phi_{Si|CALIBm|}} k_{Si|CALIBm|}$$

$$m = i$$

Equation (20a) is divided in stimulus on the left side and calibration constant and detected irradiation levels during calibration on the right side. If there is significant crosstalk between the detectors for one or more of the substances, a linear j+1 dimensional equation system with constants $(B_{|CALIBm|Si|}=) B_{mSi}$, m∈0, 1, . . . j and stimulus $Cal_{Si|CALIBm|}$ i, m∈0, 1, . . . j where $$Cal_{Si|CALIBm|} = \frac{k_{Si|CALIBm|} \Phi_{VR|CALIBm|}}{(1 - \varphi_{Si|CALIBm|})}$$

can be applied.

$$Cal_{Si|CALIBm|} = (B_{|CALIBm|Si|} \cdot \Phi_{Si|CALIBm|} =)$$
$$B_{mSi} \cdot \Phi_{Si|CALIBm|} \qquad \text{Eq(20ac),}$$

where $Cal_{Si|CALIBm|}$ is a square j+1 diagonal matrix, in which all non-main diagonal entries are zero. Generally, the tools of regression analysis tools can be applied for solving such an equation system having a plurality of variables.

A very low detected intensity of the liquid medium may be an indication that there may be no liquid medium in the test sample, e.g. that there is no flow of liquid medium through the pipe of FIG. 1. According to an embodiment of FIG. 4, an indicator of the determining unit 150, or a separate indicator 160 may be arranged to issue an alarm if the detected intensity of the liquid medium falls below a set threshold so as to be able to indicate to a controller that there may be a loss of liquid medium or even test sample in the wet part of the apparatus.

Figure 5:
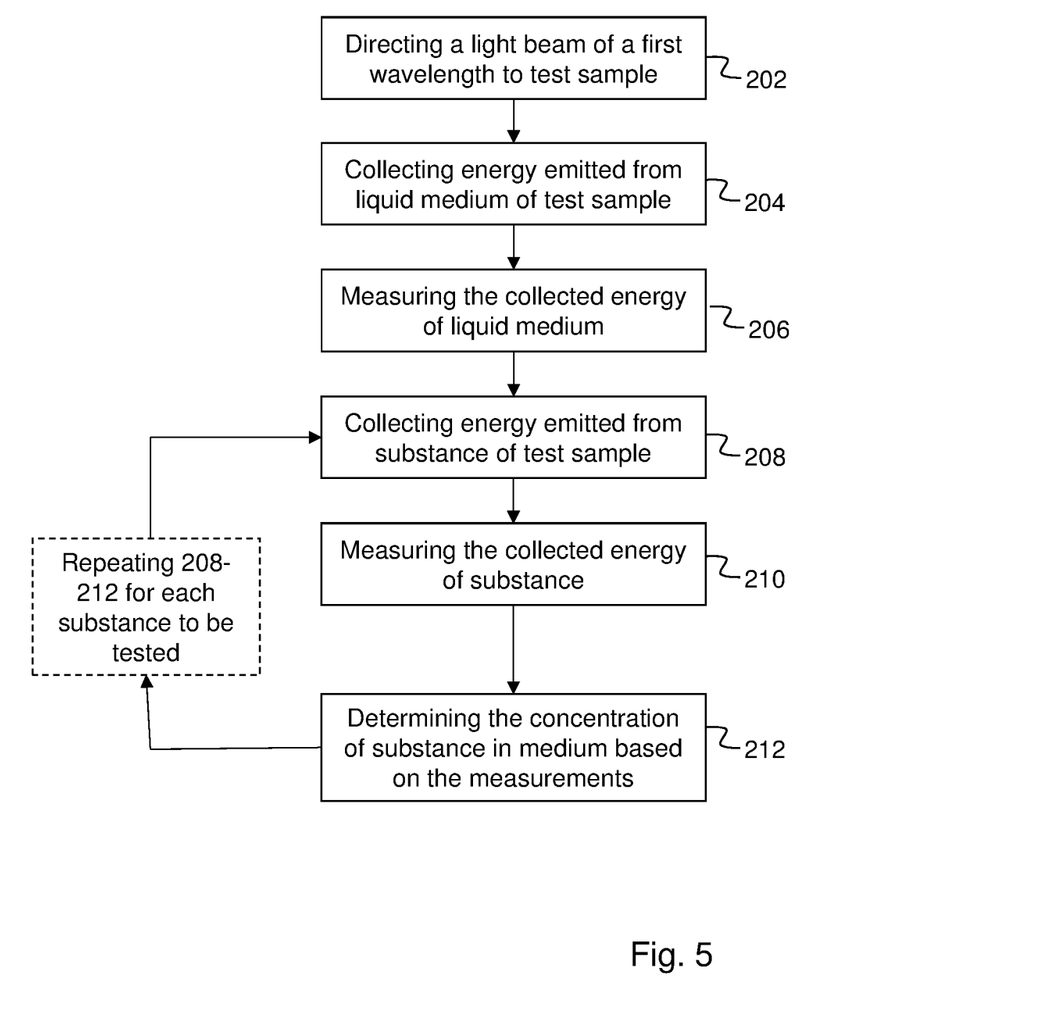
FIG. 5 is a flow chart illustrating a method according to an embodiment of the invention.

FIG. 5 is a flow chart describing a method for determining a concentration of a substance in a liquid medium of a test sample. The method comprises directing 202 a light beam of a first wavelength range towards the test sample. The method further comprises collecting 204 irradiation emitted from the liquid medium of the test sample as a result of the light beam directed towards the test sample, the irradiation being collected at one or more second wavelengths that are characteristic for the liquid medium, and measuring 206 intensity of the irradiation collected at the one or more second wavelengths. The method further comprises collecting 208 irradiation emitted from the substance of the test sample as a result of the light beam directed towards the test sample, the irradiation being collected at one or more third wavelengths that are characteristic for the substance, and measuring 210 intensity of the irradiation collected at the one or more third wavelengths. Thereafter, the method determines 212 the concentration of the substance in the liquid medium of the test sample based on the measured intensity of the irradiation collected at the one or more third wavelengths and the measured intensity of the irradiation collected at the one or more second wavelengths. Further, the irradiation collected at the one or more second wavelengths is emitted from a first surface area of the test sample and the irradiation collected at the one or more third wavelengths is emitted from a second surface area of the test sample, which first area and second area are at least partly covered by a surface area of the test sample illuminated by the light beam of the light source.

According to an embodiment, in case there are more than one substance in the liquid medium, which concentration is to be determined, the steps 210-212 may be repeated for each additional substance.

Figure 6:
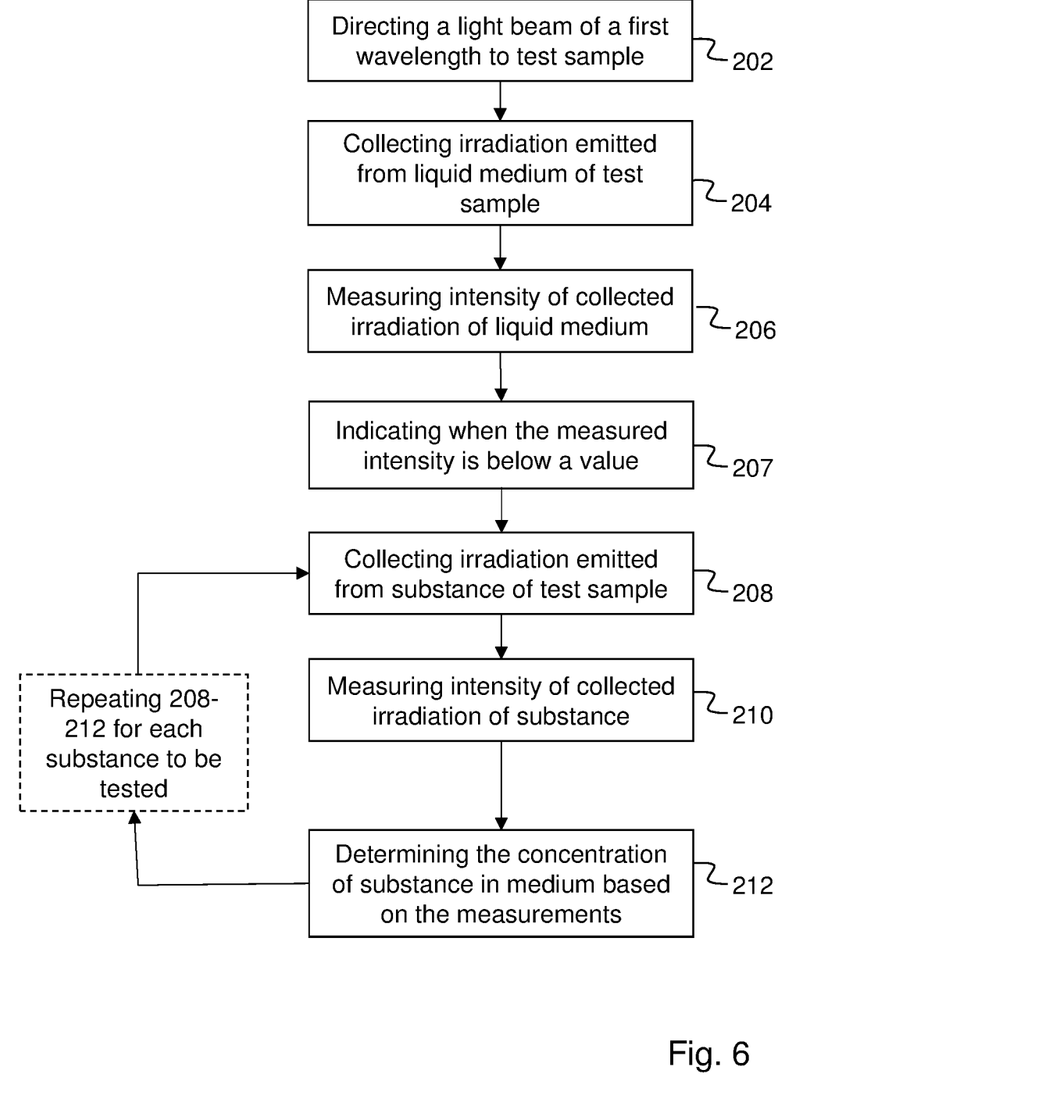
FIG. 6 is a flow chart illustrating a method according to another embodiment.

FIG. 6 shows an alternative method to the method shown in FIG. 5. This method differs from the method of FIG. 5 in that the method further comprises indicating 207 when the measured intensity of the collected irradiation of the liquid medium is below a certain value. The certain value may be set so that if the measured intensity of the irradiation collected at the one or more second wavelengths is below the certain value, it is an indication of not sufficient amount of test sample in the apparatus or an indication of possible non-reliable determination of the concentration of the substance in the liquid medium. Also, in this alternative method, the feature that the irradiation collected at the one or more second wavelengths is emitted from a first surface area of the test sample and the irradiation collected at the one or more third wavelengths is emitted from a second surface area of the test sample, which first area and second area are at least partly covered by a surface area of the test sample illuminated by the light beam of the light source, may be optional.

Although the description above contains a plurality of specificities, these should not be construed as limiting the scope of the concept described herein but as merely providing illustrations of some exemplifying embodiments of the described concept. It will be appreciated that the scope of the presently described concept fully encompasses other embodiments which may become obvious to those skilled in the art, and that the scope of the presently described concept is accordingly not to be limited. Reference to an element in the singular is not intended to mean "one and only one" unless explicitly so stated, but rather "one or more." All structural and functional equivalents to the elements of the above-described embodiments that are known to those of ordinary skill in the art are expressly incorporated herein and are intended to be encompassed hereby. Moreover, it is not necessary for an apparatus or method to address each and every problem sought to be solved by the presently described concept, for it to be encompassed hereby. In the exemplary figures, a broken line generally signifies that the feature within the broken line is optional.

The invention claimed is:

1. An apparatus for determining a concentration of a substance in a liquid medium of a test sample, the apparatus comprising:
    a light source for directing a light beam of a first wavelength range towards the test sample;
    a first detector for collecting irradiation emitted from the liquid medium of the test sample as a result of the light beam directed towards the test sample, the irradiation being collected at one or more second wavelengths that are characteristic for the liquid medium, and for measuring an intensity of the irradiation collected at the one or more second wavelengths;
    a second detector for collecting irradiation emitted from the substance of the test sample as a result of the light beam directed towards the test sample, the irradiation being collected at one or more third wavelengths that are characteristic for the substance, and for measuring an intensity of the irradiation collected at the one or more third wavelengths,
    a determining unit for determining the concentration of the substance in the liquid medium of the test sample based on the measured intensity of the irradiation collected at the one or more third wavelengths and the measured intensity of the irradiation collected at the one or more second wavelengths, the apparatus arranged such that the irradiation collected by the first detector is emitted from a first surface area of the test sample and the irradiation collected by the second detector is emitted from a second surface area of the test sample, which first surface area and second surface area are at least partly covered by a surface area of the test sample illuminated by the light beam of the light source; and further comprising an indicator for indicating when the measured intensity of the irradiation collected at the one or more second wavelengths is below a certain value.

2. The apparatus according to claim 1, wherein the first detector and the second detector are arranged such that the first surface area and the second surface area are covered by the surface area of the test sample illuminated by the light beam of the light source.

3. The apparatus according to claim 1, wherein the first surface area and the second surface area are substantially the same area.

4. The apparatus according to claim 1, wherein the first detector and the second detector are arranged symmetrically in relation to the light source.

5. The apparatus according to claim 1, wherein the apparatus is arranged so that the first detector and the second detector receives irradiation emitted from the test sample at one and the same direction.

6. The apparatus according to claim 5, wherein the apparatus is arranged so that there is a zero degree angle between the light beam directed towards the test sample and the irradiation emitted from the test sample that is received by the first detector and the second detector.

7. The apparatus according to claim 1, wherein the first detector is further adapted to collect irradiation and measure intensity of the irradiation at the second wavelength, the irradiation being emitted from a reference sample comprising a known concentration of the substance in the liquid medium, and the second detector is further adapted to collect irradiation and measure intensity of the irradiation at the third wavelength, the irradiation being emitted from the reference sample, and the determining unit is further adapted to determine the concentration of the substance in the liquid medium of the test sample based also on the measured intensity of the irradiation collected at the second wavelength from the reference sample and on the measured intensity of the irradiation collected at the third wavelength from the reference sample.

8. The apparatus according to claim 1, further comprising a temperature sensor for detecting the temperature of the test sample, and wherein the determining unit is arranged for determining the concentration of the substance in the liquid medium of the test sample further based on the detected temperature of the test sample.

9. The apparatus according to claim 1, wherein the liquid medium is water and the substance is oil.

10. The apparatus according to claim 1, wherein the certain value is set so that when the measured intensity of the irradiation collected at the one or more second wavelengths is below the certain value, it is an indication of possible low concentration determining accuracy of the apparatus.

11. The apparatus according to claim 1, wherein the indicator is arranged for indicating when the measured intensity of the irradiation collected at the one or more second wavelengths is below a certain value by issuing an alarm signal.

12. The apparatus according to claim 1, wherein the indicator is arranged for indicating when the measured intensity of the irradiation collected at the one or more second wavelengths is below a certain value by triggering a correction of a process flow system from which process flow the test sample is taken.

13. A method for determining a concentration of a substance in a liquid medium of a test sample, the method comprising:
   directing a light beam of a first wavelength range towards the test sample;
   collecting irradiation emitted from the liquid medium of the test sample as a result of the light beam directed towards the test sample, the irradiation being collected at one or more second wavelengths that are characteristic for the liquid medium;
   measuring an intensity of the irradiation collected at the one or more second wavelengths;
   collecting irradiation emitted from the substance of the test sample as a result of the light beam directed towards the test sample, the irradiation being collected at one or more third wavelengths that are characteristic for the substance;
   measuring an intensity of the irradiation collected at the one or more third wavelengths,
   determining the concentration of the substance in the liquid medium of the test sample based on the measured intensity of the irradiation collected at the one or more third wavelengths and the measured intensity of the irradiation collected at the one or more second wavelengths, the method being wherein the irradiation collected at the one or more second wavelengths is emitted from a first surface area of the test sample and the irradiation collected at the one or more third wavelengths is emitted from a second surface area of the test sample, which first surface area and second surface area are at least partly covered by a surface area of the test sample illuminated by the light beam of the light source; and further comprising: indicating when the measured intensity of the irradiation collected at the one or more second wavelengths is below a certain value.

14. A method according to claim 13, wherein there are a plurality of substances in the liquid medium of the test sample, and the method further comprises repeating the collecting and the measuring of intensities at the one or more third wavelengths for wavelengths characteristic for each of the plurality of substances, and the determining of the concentration of the plurality of substances in the liquid medium, for each of the plurality of substances.

* * * * *